United States Patent [19]
Hammock et al.

[11] Patent Number: 5,985,269
[45] Date of Patent: Nov. 16, 1999

[54] BACULOVIRUS INSECT CONTROL COMPOSITIONS WITH ENHANCED LETHALITY

[75] Inventors: Bruce D. Hammock, Davis, Calif.; Kelli Hoover, Pennsylvania Furnace, Pa.; Sean S. Duffey, *deceased, late of Davis, Calif., by* Anne Duffey, *legal representative*

[73] Assignee: The Regents of the University of California, Oakland, Calif.

[21] Appl. No.: 09/073,745

[22] Filed: May 6, 1998

[51] Int. Cl.$^6$ ...................................................... A01N 63/00
[52] U.S. Cl. ......................................... 424/93.6; 424/93.2
[58] Field of Search .................................... 424/93.6, 93.2

[56] References Cited

PUBLICATIONS

Hoover et al., "Influence of Induced Plant Defenses in Cotton and Tomato on the Efficacy of Baculoviruses on Noctuid Larvae," *J. Chem. Ecol.*, 24(2), pp. 253–271 (1998).
Hoover et al., "Effects of Plant Identity and Chemical Constituents on the Efficacy of a Baculoviruses Against *Heliothis virescens*," *J. Chem. Ecol.*, 24(2), pp. 221–252 (1998).
Ignoffo and Garcia, "Antioxidant and Oxidative Enzyme Effects on the Inactivation of Inclusion Bodies of the Heliothis Baculovirus by Simulated Sunlight–UV," *Environ. Entomol.*, 23(4), pp. 1025–1029 (1994).
Halliwell et al., "The Deoxyribose Method: A Simple 'Test–Tube' Assay for Determination of Rate Constants for Reactions of Hydroxyl Radicals," *Anal. Biochem.*, 165, pp. 215–219 (1987).
Halliwell et al., "Methods for the Measurement of Hydroxyl Radicals in Biochemical Systems: Deoxyribose Degradation and Aromatic Hydroxylation," *Methods of Biochemical Analysis*, 33, pp. 59–90.
Wu et al., "Propyl Gallate as a Hepatoprotector in vitro and in vivo," *Biochem. Pharm.*, 48(2), pp. 419–422 (1994), abstract only.

*Primary Examiner*—Jean C. Witz
*Attorney, Agent, or Firm*—Majestic, Parsons, Siebert & Hsue P.C.

[57] ABSTRACT

A method of enhancing baculovirus disease in pests on a crop is provided through an insect control composition by applying an insect control composition to the crop. The applied composition includes a baculovirus that is infectious for at least one pest feeding on the crop and an enhancing agent for the baculovirus. The enhancing agent is preferably administered so as to be ingestible by the pest together with the baculovirus. A preferred enhancing agent is mannitol which increases the mortality of larval tobacco budworms feeding on cotton when infected with *Autographa californica* by 238%.

31 Claims, 1 Drawing Sheet

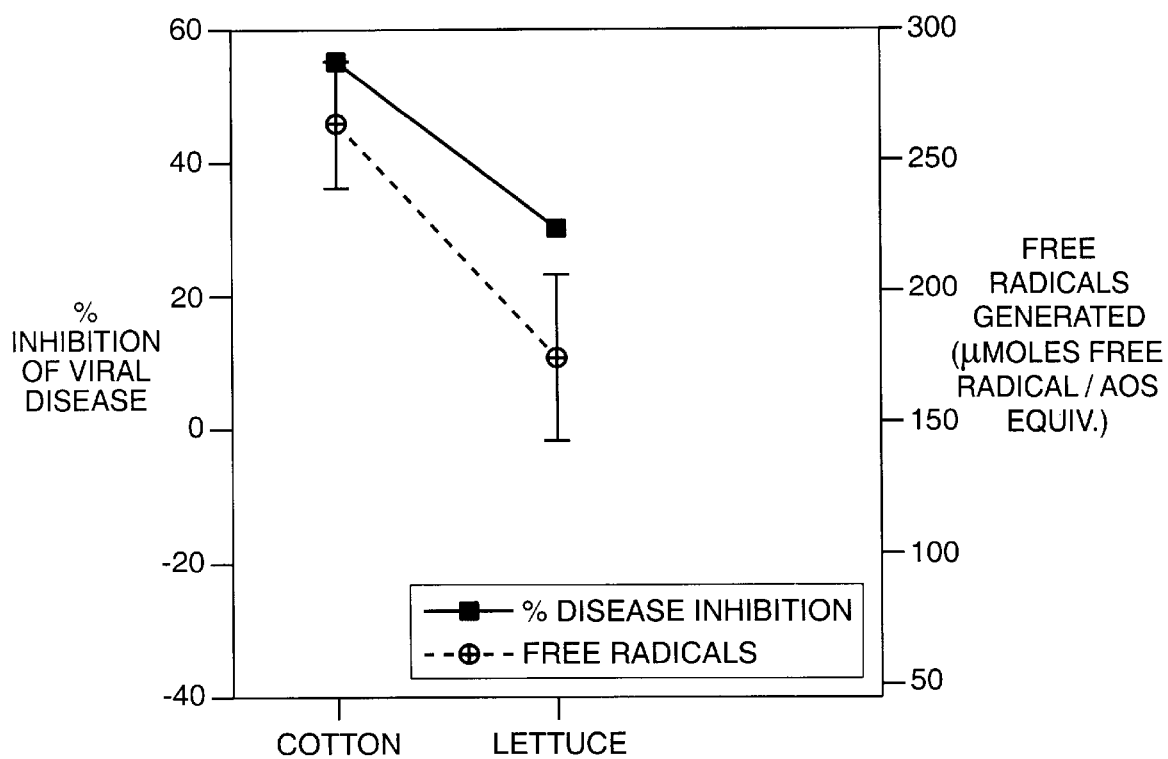
FIG._1

BACULOVIRUS INSECT CONTROL COMPOSITIONS WITH ENHANCED LETHALITY

FIELD OF THE INVENTION

The present invention generally relates to uses of baculoviruses for insect control, and more particularly to insect control compositions including baculoviruses with significantly enhanced pest mortality for commercially practical use on crops such as cotton.

BACKGROUND OF THE INVENTION

The lepidopteran family Noctuidae includes some of the most destructive agricultural pests, such as the genera Heliothis, Helicoverpa, Spodoptera, and Trichoplusia. For example, included in this family are the tobacco budworm (*Heliothis virescens*), the cotton bollworm (*Helicoverpa zea*), the cotton leafworm (*Alabama argillacea*), the spotted cutworm (*Amathes c-nigrum*), the glassy cutworm (*Crymodes devastator*), the bronzed cutworm (*Nephelodes emmedonia*), the fall armyworm (*Spodoptera frugiperda*), the beet armyworm (*Spodoptera exigua*), and the variegated cutworm (*Peridroma saucia*).

Baculoviruses are arthropod-specific, double stranded DNA viruses that can be used to control insect pests. The nuclear polyhedrosis viruses ("NPV") are one baculovirus subgroup. On the order of forty nuclear polyhedrosis viruses have been isolated from insect species. (See, for example, *Atlas of Invertebrate Viruses,* Adams and Bonami, editors, CRC Press, Inc., 1991.) Various baculoviruses, including those that infect cotton bollworm, *Helicoverpa zea,* tobacco budworm, *Heliothis virescens,* Douglas fir tussock moth, *Orygia pseudotsugata,* gypsy moth, *Lymantria dispar,* alfalfa looper, *Autographa californica,* European pine sawfly, *Neodiiprion sertifer,* and codling moth, *Cydia pomonella,* have been registered as pesticides.

A characteristic feature of the NPV group is that many virions are embedded in a crystalline protein matrix referred to as an "occlusion body." Examples of NPVs include *Lymantria dispar* NPV (gypsy moth NPV), *Autographa californica* MNPV, *Anagrapha falcifera* NPV (celery looper NPV), *Bombyx mori* NPV, *Spodoptera littoralis* NPV, *Spodoptera frugiperda* NPV, *Heliothis armigera* NPV, *Mamestra brassicae* NPV, *Choristoneura fumiferana* NPV, *Trichoplusia ni* NPV, *Helicoverpa zea* NPV, and *Rachiplusia ou* NPV. For field use, occluded viruses often are preferable due to their greater stability since the viral occlusion body provides protection for the enclosed infectious nucleocapsids.

Recombinant baculoviruses are also known and useful as insect control compositions. For example, U.S. Pat. No. 5,674,747, issued Oct. 7, 1997, inventors Hammock et al., describes recombinant baculoviruses in which a mutated JHE juvenile hormone esterase) coding sequence provides relatively rapid speed of kill in insects. U.S. Pat. No. 5,674,485, issued Oct. 7, 1997, inventors Hammock et al., describes a recombinant expression vector capable of expression in a host insect and including a coding sequence for JHE that, when expressed, lacks the signal sequence targeting the enzyme to the plasma membrane. U.S. Pat. No. 5,643,776, issued Jul. 1, 1997, inventors Hammock et al., describes recombinant baculoviruses with a mutated JHE coding sequence. McCutchen et al., *Bio/Technology,* 9, pp. 848–852 (1991), reports the construction of a recombinant, polyhedron-positive *Autographa californica* NPV that expresses an insect-selective toxin (AaIT), which is isolated from the scorpion *Androctonus australis*. Copending application Ser. No. 08/435,040, filed May 8, 1995, inventors Hammock et al, describes a method to accelerate the rate of pest kill by treating the pests or their loci with at least two different insect toxins, which are expressed from at least one recombinant microbe such as a baculovirus.

However, a limitation of the use of baculoviruses for pest control has been that their efficacy can be adversely affected by host-plant chemicals and they can also be inactivated by sunlight. The influence of host plants on the course and severity of baculovirus disease in insects has been discussed, for example, by Felton et al. *J. Chem. Ecol.,* 13, pp. 947–957 (1987), *J. Chem. Ecol.,* 16, pp. 1211–1236 (1990), and *Arch. Insect Biochem. Physiol,* 29, pp. 187–197 (1995). Ignoffo and Garcia, *Environmental Entomology,* 23, pp. 1025–1029 (1994), have studied the inactivation of microbial insecticides by exposure to sunlight. They found that propyl gallate provided the best protection of *Baculovirus heliothis* (of three anti-oxidants tested) and catalase the best of three oxidative enzymes tested. They suggested that reactive radicals generated by sunlight can cause inactivation of field-applied viral and other microbial insecticides. Unfortunately, they acknowledged that the materials they had used could not be used practically to provide UV protection of commercial microbial insecticides.

SUMMARY OF THE INVENTION

It is an object of the present invention to substantially enhance the mortality of insect pests that ingest baculoviruses during feeding on crop foliage.

In one aspect of the present invention, a method of enhancing baculovirus disease in pests on a crop is provided by applying an insect control composition to the crop. The applied composition includes at least one baculovirus species and a baculovirus disease enhancing agent. The at least one baculovirus species is preferably in the form of polyhedral occlusion bodies and can be a mixture of wild-type and/or recombinant. The enhancing agent is preferably administered so as to be ingestible by the pest together with baculovirus as the pest feeds on the crop, and preferably is in an amount effective to increase pest mortality by at least about 100% with respect to ingestion of the baculovirus alone.

A particularly preferred embodiment of the invention is wherein mannitol is used as an enhancing agent. When mannitol was applied in combination with a baculovirus infectious for tobacco budworm, then larval tobacco budworms feeding on cotton had mortality increased by 238%.

BRIEF DESCRIPTION OF THE DRAWING

FIG. 1 graphically illustrates the percent of viral disease inhibition when larvae of tobacco budworm (*Heliothis virescens,* feeding on cotton or lettuce) was infected with *Autographa californica* AcMNPV.

DETAILED DESCRIPTION OF THE PREFERRED EMBODIMENTS

We have discovered that the susceptibility of noctuidae larvae to baculovirus infection is inhibited in large part by phenolic oxidation by phenolases, particularly peroxidase (POD), which subsequently generates free radicals in the foliage being ingested by the infected pest. The more free radicals generated, the lower the incidence of viral disease, particularly when the crop is cotton.

With reference to FIG. 1, one can see that baculovirus insecticides do not perform well for controlling noctuid pests on a crop such as cotton. The viral disease is almost 60% inhibited compared with larvae fed on diet or iceberg lettuce. The diminished efficacy of baculoviruses on a crop such as cotton is the result of free radicals generated during the simultaneous ingestion of plant foliage with viral particles by the host insect. Free radical generation leading to inhibition of viral disease is mediated, at least in part, by POD.

We developed an assay for the detection of free radicals in plant foliage in the immediate aftermath of an oxidative burst. Assessment of free radical generation, such as in an assay of crushed foliage, is a useful predictor of the inhibition of baculoviruses as pest control agents on plants. Cotton appears to be particularly inhibitory to baculovirus disease, perhaps as a consequence of complex redox cycling in the plant.

The present invention provides combinations of baculoviruses with baculovirus disease enhancing agents that overcome the inhibitory effect in crop foliage, particularly for a crop such as cotton. Because baculoviruses do not at present provide adequate control on crops such as cotton, and since cotton is a major crop worldwide, the present invention is of considerable practical importance to enhance baculovirus insecticides on a crop such as cotton.

Broadly, the invention comprises administering an insect control composition to the crop for pest control where the composition includes at least one baculovirus species and a baculovirus disease enhancing agent. The baculovirus species in the insect control composition preferably is in the form of polyhedral occlusion bodies, since the viral occlusion body provides protection for the enclosed infectious nucleocapsids during field applications. Of particular interest for a crop such as cotton are the baculoviruses that infect cotton bollworm (*Helicoverpa zea*) and tobacco budworm (*Heliothis virescens*).

In practicing the present invention, at least one baculovirus species is used. More than one baculovirus species can be used so as to increase the insecticidal effects against a wider variety of insects. Such combinations of baculoviruses are known to the art. For example, Maeda et al. in European Patent Application Publication No. 0 225 777, published Jun. 16, 1987, discloses a recombinant virus containing DNA segments of both of two species of viruses for which their host insects differed. U.S. Pat. No. 5,071,748, issued Dec. 10, 1991, inventor Miller, discloses mixtures of baculoviruses. U.S. Pat. No. 5,756,340, issued May 26, 1998, Ser. No. 08/435,040, filed May 8, 1995, inventors Hammock et al., discloses insect control through combinations of insecticidal recombinant microbes.

The one or more baculoviruses of the inventive insect control composition may each be wild-type, may be recombinant, or may be mixtures of wild-type and recombinant. Where more than one baculovirus is used, then one usually will choose the combination so as to avoid the two infecting the same insect. This is because such usually can lead to interference between the baculoviruses and consequently decreased lethality; however, there are instances where there can be complementarity in mixtures of baculoviruses where both infect the same insect.

Among suitable recombinant baculoviruses are those expressing a scorpion toxin, such as the excitatory toxin from *Androctonus australis* (AaIT) or from *Leuirus quinquestriatus hebraeus* (LqhαIT), such as are described by Hammock et al. in U.S. Pat. No. 5,756,340, issued May 26, 1998, Ser. No. 08/435,040, McCutcheon et al., *Bio/Technology*, 9, pp. 848–852 (1991), and Maeda et al., "Insecticidal Effects of an Insect-Specific Neurotoxin Expressed by a Recombinant Baculovirus," *Virology*, 184, pp. 777–780 (1991). These latter two illustrate construction of a recombinant baculovirus expressing AaIT.

The greatest inhibition of disease in the field appears to occur at lower viral doses. Growers typically apply a very high viral dose ($LD_{99}$) initially, but production costs will limit the amount of virus that can be commercially applied. As will be discussed further, even small amounts of the enhancing agents of the invention will be effective at substantially any viral dose. In other words, enhancing agents of the invention are effective even at lower viral doses (such as $LD_{25}$) where the greatest inhibition of disease caused by the plant occurs.

The second essential component of the present invention is a baculovirus disease enhancing agent which is administered either simultaneously with the baculovirus or baculovirus mixture (such as in an admixture of baculovirus occlusion bodies) or is administered within about three hours prior to application of baculovirus to the crop for which pest control is desired.

Many of the preferred enhancing agents for practicing this invention are anti-oxidants; however, although Ignoffo and Garcia, supra, had found that propyl gallate (an anti-oxidant) protected the baculovirus heliothis (HzSNPV) against sunlight, we have found substantially no protection of baculovirus from inhibition by propyl gallate. Ignoffo and Garcia also had found some efficacy with the oxidative enzyme catalase; however, although we found that catalase did provide some enhancement when applied with baculovirus to cotton foliage, the enhancement was only about 68% compared with untreated cotton.

Although an anti-oxidant (such as propyl gallate) or an oxidative enzyme (such as catalase) may inhibit sunlight inactivation of viral pesticides when these compounds are admixed with occlusion bodies and then exposed to fluorescent lamps, such conditions are quite different from those that occur in the field when caterpillars ingest polyhedrin occlusion bodies along with the crop foliage. For one example, pest caterpillars typically have a stomach pH of about 9. Thus it is not surprising that the work of Ignoffo and Garcia with simulated sunlight would not be predictive of results when agents, in combination with baculoviruses, are ingested together with crop foliage. In order to determine whether enhancing agents are useful for purposes of the present invention, they can be assessed, without undue experimentation, for free radical generation, such as in the assay using crushed foliage that will be more fully described hereinafter. Thus, one can reasonably predict that hydroxyl scavengers, and other similar free radical scavengers, will be useful as enhancing agents in practicing the present invention.

Disease enhancing agents of the invention are in an amount substantially to increase post mortality, preferably in an amount effective to increase pest mortality by at least about 100% (with respect to pest mortality from administration of the baculovirus species without enhancing agents). Enhancing agents suitable for practice of the present invention fall into several functional types (which can overlap in function).

One type is free radical scavengers, particularly hydroxyl radical scavengers, which normally will need to be effective in the pest gut. This type includes polyhydroxy compounds. Thus, polyhydroxy compounds such as glucose, sucrose, lactose, ribose, galactose, and mannitol are useful enhancing agents. Particularly preferred is mannitol. Other suitable hydroxyl radical scavengers can be screened by methods well known to the art. For example, Halliwell et al., *Analytical Biochemistry*, 165, pp. 215–219 (1987) describe a simple assay for determining reactions of reagents with hydroxyl radical scavenging function. Halliwell et al. further describe measurements of hydroxy radicals in biochemical systems, *Methods of Biochemical Analysis*, 33, pp. 59–90.

Another type of enhancing agent for practicing the invention is a chelating agent, for example, those agents which are effective to chelate with phenolic in the pest gut. Among suitable chelating agents are sodium borate, or metal chelators such as thiourea.

We have also found that some anti-oxidants can provide good inhibition retardation, including ascorbate, and most notably butylated hydroxy anisole and butylated hydroxy toluene (BHA and BHT, respectively).

The invention will now be illustrated by the following examples, which are intended to illustrate but not to limit the subject invention.

EXAMPLE 1

The free radicals causing baculoviral disease inhibition include active oxygen species (AOS). This example includes the description of an assay for measuring AOS in crushed foliage.

Using a homemade leaf press that crushes a moistened leaf between two solid metal cylinders turning in unison (designed by T. L. German, University of Wisconsin), the pressed-leaf-extract was collected from each pre-weighed leaf sample as it was washed with 2.5 ml of a 0.02% solution of methemoglobin in pH 7 buffer into a 20 ml scintillation vial. The cylinders of the leaf press were washed with distilled water between samples. Immediately after collecting the pressed-leaf-extract, the sample was placed in an Eppendorf™ tube followed by centrifugation at 14,000 rpm for 3–5 seconds to precipitate remaining leaf material. The supernatant was immediately transferred to a 1.5 ml cuvette and the absorbance read at 406 nm against a buffer blank. Samples were incubated for 1 hour in the dark. After 1 hour, the absorbance was read again. Because oxidation of the phenolic compounds from the pressed-leaf-extract occurs during the incubation period by the enzymes released by crushing, we also read the initial and final absorbances of samples in the absence of heme. The increase in absorbance due to oxidation was subtracted from the decrease in absorbance obtained from heme.

To determine the amount of AOS/free radicals generated in each sample, the difference between the initial absorbance and the final absorbance was corrected for leaf weight to obtain the change in absorbance/g of leaf tissue. This value was entered into the equation for the standard curve to quantify free radical generation in μmoles free radical/AOS equivalents.

Leaves of cotton and lettuce were divided into equal pieces. Each chemical treatment was applied to a piece of the same leaf Because tomato has 5–7 leaflets/leaf, rather than cutting the leaf, one leaflet from each leaf was used as a control. All leaf pieces and leaflets were weighed prior to crushing. For each chemical treatment applied to foliage in bioassays (described below), 25 μl of a test chemical solution was first added to the scintillation vial used to collect the pressed-leaf-extract. Samples were also run in the absence of heme to permit correction for oxidation as described above. Free radical generation in crushed cotton, lettuce, and tomato foliage were reported as the mean±SE of four replicates.

Eggs of tobacco budworm (*H. virescens*) and corn earworm (*H. zea*) were obtained from the USDA/ARS (Stoneville, Miss.). Neonate larvae were reared to third instar on semi-synthetic diet (Southland Products, Lake Village, Ark.) in 24-well tissue culture plates (Fisher) at 26±1° C. and 16L:8D. Within 6 hours after molting to the third instar, larvae were transferred to empty 24-well tissue culture plates for 24 hours to void their gut.

*Autographa californica* M nuclear polyhedrosis virus (AcMNPV, C6 clone) (Ayers et al., 1994) and *Helicoverpa zea* S NPV (HzSNPV, original isolate plaque purified from Elxar™, Sandoz-Wander (Wasco, Calif.)) were amplified in larvae of *H. virescens* and *H. zea,* respectively, extracted, partially purified, and stored until use.

Plants were used at the 4–5 leaf stage. A leaf was randomly removed from each of 16 plants. Using a No. 3 cork borer, 0.65 $cm^2$ leaf disks were cut from each leaf and placed in petri dishes partially filled with 2.4% agar. Leaf disks were distributed such that each chemical treatment would be applied to three disks from each plant. Gelatin/chemical mixtures were prepared by dissolving Knox™ gelatin in 0.1M potassium phosphate buffer pH 7 at 50%C at a concentration of 4% for cotton and 6% for lettuce and tomato. After cooling at 37° C., test chemicals were added to the gelatin as described in Wolfson and Murdock (1987). For treatments involving application of semi-purified POD to foliage, an additional control included boiling the enzyme for 15 minutes before mixing with gelatin. On lettuce, semi-purified POD was applied at four doses (125, 62.5, and 31.25 μg/ml and 100, 62.5, 31.25, and 15.6 μg/ml, respectively) to evaluate whether inhibition of disease responded in a dose-dependent manner. Ten μl of each gelatin/chemical mixture at 35–37° C. were applied to each leaf disk with a pipette and distributed evenly with a fine paint brush. Each treatment mixture was applied to a group of 48 leaf disks. After drying at ambient temperature (≈30 minutes), a viral formulation was applied to each leaf disk.

AcMNPV was tested on cotton and lettuce against *H. virescens*; whereas, HzSNPV was tested on tomato against *H. virescens* and *H. zea*. Polyhedral occlusion bodies (OBS) were suspended at a single concentration (30 OBS/μl for AcMNPV and 3 OBS/μl for HzSNPV) in milliQ $H_2O$ for application in 1 μl aliquots to each leaf disk. We used a low dose because we suspect that lower vial doses are probably more biologically relevant (Duffey et al., 1995). The dose for each replicate was determined by treating a group of insects on small cubes (8 $mm^3$) of artificial diet. Viral inoculum was allowed to dry at ambient temperature. Once the viral solution was dry, leaf disks were placed one per well in 24-well tissue culture plates partially filled with 2.4% agar. A starved larva was then transferred one to a well so that each larva received a single leaf disk. After 18 hours, insects that had consumed an entire treated leaf disk or artificial diet were transferred individually to excess diet in 35 ml cups and maintained until death or pupation at 26±1° C. and 16L:8D. A group of control insects was treated with 80 μM sodium borate in the absence of virus to ensure that this chemical was not toxic to the larvae at this concentration. Mortality was scored at 8–9 days post-infection.

The effect of chemical applications to foliage on subsequent phenolase activities was examined using a portion of 8 of the 16 leaves used for bioassay. Final concentrations of test chemicals prepared in gelatin and applied to leaves were determined by measuring the amount of gelatin that remained on the leaf disk after handling just prior to being fed to larvae. A 0.1% solution of rose bengal (Sigma) was mixed with gelatin and applied to 10 leaf disks from each plant species as described above. After drying, leaf disks were placed in 0.1M K phosphate buffer and stirred with gentle heating to wash all the gelatin off the leaf disks. Absorbances were read at 496 nm, which is the peak of the visible spectrum for rose bengal. The mean amount of gelatin that stuck to the leaves was calculated based on a standard curve. On cotton, tomato, and lettuce, 5.88±0.36, 4.58±0.36, and 4.08±0.13 µl of the 10 µl of the gelatin mixture applied to leaf disks still remaining at the time they were fed to larvae.

Survival data were analyzed by logistic regression. In addition, we compared the frequency of dead with alive insects between selected treatments using data pooled from the two replicates by Chi-square analysis with Bonferroni's correction for the number of paired comparisons (Steel and Torrie, 1980). We pooled all data for analyses as the mortality levels characterized by artificial diet showed considerable variation between replicates.

We regressed total percent mortality for each treatment on each plant species as a function of mean free radical generation (as µmole free radical/AOS equivalents) (Steel and Torrie, 1980). Free radicals were assayed using the same plant cultivars under the same conditions as the bioassay on a different day. We regressed mean free radical generation for each foliar treatment as a function of man foliar POD activity for each treatment. This analysis was performed on pooled data.

We tested our ability to reverse the effects of POD activity and/or free radical generation as inhibitors of viral disease by applying a variety of antioxidants to foliage. On tomato, all antioxidants were applied in combination with POD because tomato by itself is not inhibitory to the virus.

All antioxidants tested enhanced viral disease on at least one plant species. For example, ascorbate completely inhibited all phenolase activity when applied to cotton or tomato foliage. On cotton and tomato, mortality increased 63% ($x^2$=2.0, p=0.1499, n=169) and 432% (11, p=0.0079, n=180), respectively. We could not assess accurately the impact of ascorbate on free radical generation, however, because free radicals increase markedly in the presence of $Fe^{2+}$ giving ambiguous results (Koppenol and Butler, 1985).

Application of mannitol, a OH. radical scavenger, provided the best protection of all antioxidants tested on cotton. Mannitol did not affect cotton POD activity, but did inhibit free radical generation and enhance larval mortality compared to untreated cotton foliage by 238% (Table 1; $x^2$=13, p=0.0003, n=172).

Table 1 summarizes the effects of applying enhancing agents in accordance with the invention to cotton foliage. The pest larvae was H. virescens, which ingested baculovirus (AcMNPV) in conjunction with a control (gelatin only) or in conjunction with an enhancing agent of the invention.

TABLE I

| Cotton Foliage (with AcMNPV) | % Mortality of Pest |
|---|---|
| Control | 13 |
| Mannitol (20 µM) | 44 |
| Sodium borate (80 µM) | 41 |
| BHT (20 µM) | 38 |
| Lutein (0.4 µM) | 25 |

Application of BHT enhanced viral disease on all tested plants, bringing the percent mortality to the level of that obtained on artificial diet or higher. For example, mortality on cotton increased 186% following application of BHT ($x^2$=13.0, p=0.003, n=179). On tomato, BHT increased mortality by 263% ($x^2$=7.0, p=0.0081, n=168). BHT also inhibited POD and free radical activities in all tested plant species.

Lutein, a water soluble analog of β-carotene, did not scavenge free radicals as effectively as BHT based on the heme assay, but was fairly effective at reversing free radical inhibition of viral disease. Lutein moderately inhibited free radical generation in cotton (49%), but was only mildly inhibitory in tomato (15%) and lettuce (32%). As a consequence of lutein application, viral disease was enhanced on cotton by 91% relative to the control such that mortality approached that obtained on artificial diet (25% compared with 30% on diet). Addition of lutein plus cotton POD to tomato allowed mortality to nearly reach the level on untreated control foliage (mortality for POD added to tomato without lutein was 6.25%).

Borate, which forms a chelate with catecholic phenolics, was tested on cotton and lettuce foliage. Application of borate, however, markedly enhanced viral disease on cotton by 215% ($x^2$=11, p=0.0008, n=178); free radical generation was not affected based on the heme assay. On lettuce borate inhibited POD activity, yet free radical generation increased according to the heme assay. None of the insects died that were treated with the same concentration of borate applied to lettuce in the absence of virus.

EXAMPLE 2

An experiment analogous to that as described in Example 1 was repeated, but instead of the AcMNPV baculovirus for testing on cotton and lettuce or HzSNPV for testing on tomato, a recombinant baculovirus was utilized (AcAaIT).

A group of antioxidants were applied to cotton using the recombinant AcAaIT. The same results were seen as with the wild-type viruses. Third-instar larvae of Heliothis virescens were treated with 30 occlusion bodies/larva of AcAaIT (the recombinant expressing a neurotoxin from a scorpion) where the treatments to the leaf were (1) gelatin (control), (2) application of a free radical generator (1% quebracho tannin), or (3) application of 100 µM ascorbate (a reducing agent and free radical scavenger which works sometimes, but not always). Percentage mortality of 50 larvae in each group were as follows:

Control: 10%

Application of Tannins: 0%

Application of Ascorbate: 30.4% (a 3-fold improvement in performance of the virus with the addition of an antioxidant).

It is to be understood that while the invention has been described above in conjunction with preferred specific embodiments, the description and examples are intended to illustrate and not limit the scope of the invention, which is defined by the scope of the appended claims.

It is claimed:

1. A method of enhancing baculovirus disease in pests on a crop, comprising:
   administering an insect control composition to the crop for pest control thereof, the composition including (1) at least one baculovirus species and (2) a baculovirus disease enhancing agent, the enhancing agent being administered before or with the baculovirus species and being in an amount effective to increase pest mortality with respect to pest mortality from administration of the baculovirus species without the presence of enhancing agent.

2. The method as in claim 1 wherein the enhancing agent increases pest mortality by at least about 100%.

3. The method as in claim 2 wherein the enhancing agent is a free radical scavenger.

4. The method as in claim 3 wherein the enhancing agent is administered so as to be ingestible by the pest, and the enhancing agent is effective to scavenge free radicals in the pest gut.

5. The method as in claim 3 wherein the crop is cotton.

6. The method as in claim 5 wherein the enhancing agent is a polyhydroxy compound.

7. The method as in claim 2 wherein the enhancing agent includes mannitol.

8. The method as in claim 5 wherein the enhancing agent is administered so as to be ingestible by the pest, and the enhancing agent is effective to chelate with phenolics in the pest gut.

9. The method as in claim 2 wherein the enhancing agent includes sodium borate.

10. The method as in claim 2 wherein the enhancing agent includes butylated hydroxyanisole, butylated hydroxy toluene, or mixtures thereof.

11. The method as in claim 2 wherein the enhancing agent is a hydroxyl radical scavenger and is in a concentration in the administered insect control composition of from about 100 $\mu$M to about 100 mM.

12. A method for enhancing baculovirus disease in pests feeding on a crop, comprising:

administering an insect control composition to the crop for pest control thereof, the composition including (1) at least one baculovirus species and (2) a baculovirus disease enhancing agent, the enhancing agent being ingestible by the pest in conjunction with the baculovirus species and being in an amount effective to increase pest mortality by at least about 100% with respect to ingestion of baculovirus species alone.

13. The method as in claim 12 wherein the enhancing agent is effective as a free radical scavenger in the pest gut.

14. The method as in claim 12 wherein the at least one baculovirus species and the baculovirus disease enhancing agent are in an admixture, and the administering includes applying the admixture to the crop foliage.

15. The method as in claim 12 wherein the crop is cotton.

16. The method as in claim 13 wherein the enhancing agent is a polyhydroxy compound.

17. The method as in claim 15 wherein the enhancing agent includes mannitol.

18. The method as in claim 15 wherein the enhancing agent includes sodium borate.

19. The method as in claim 15 wherein the enhancing agent includes butylated hydroxyanisole, butylated hydroxy toluene, or mixtures thereof.

20. The method as in claim 12 wherein the enhancing agent is a hydroxyl radical scavenger, and the crop is cotton.

21. A method for enhancing baculovirus disease of noctuid larvae on cotton comprising:

administering an insect control composition to cotton foliage, the insect control composition including occlusion bodies of at least one baculovirus species infectious for noctuid larvae, and a disease enhancing agent for said baculovirus species when the insect pest is infected therewith, the occlusion bodies being administered to the foliage (a) simultaneously with the enhancing agent, or (b) within about three hours subsequent to the enhancing agent.

22. The method as in claim 21 wherein the at least one baculovirus species is effective in infecting *Heliothis virescens* or *Helicoverpa zea* larvae.

23. The method as in claim 21 wherein the enhancing agent is effective in inhibiting peroxidase or peroxidase reaction products in the pest gut.

24. The method as in claim 23 wherein the enhancing agent is an hydroxyl radical scavenger.

25. The method as in claim 21 wherein the enhancing agent includes mannitol.

26. The method as in claim 23 wherein the enhancing agent forms chelates with phenolics.

27. The method as in claim 21 wherein the insect control composition is administered in a viral dose of at least about the $LD_{25}$ for the noctuid larvae.

28. The method as in claim 21 wherein the at least one baculovirus species expresses the disease enhancing agent as a foreign gene product.

29. The method as in claim 28 wherein the expression of the foreign gene is of a peroxidase inhibitor, a free radical scavenger, or a quinone trapping agent, or a reducing agent.

30. A method of controlling pests on cotton, comprising:

administering an insect control composition to cotton foliage, the insect control composition including occlusion bodies of at least one baculovirus species infectious for a cotton pest, and a disease enhancing for the baculovirus when infecting the cotton pest, the disease enhancing agent including mannitol, sodium borate, BHT, BHA, ascorbate, or mixtures thereof in an amount from about 100 $\mu$M to about 500 mM.

31. The method as in claim 30 wherein the baculovirus species is one or more of *Anagrapha falcifera, Anticarsia gemmatalis, Autographa californica, Buzura suppressuria, Cydia pomonella, Helicoverpa zea, Heliothis armigera, Manestia brassicae, Plutella xylostella, Spodoptera exigua, Spodoptera littoralis, Spodoptera litura,* and recombinants thereof.

* * * * *